United States Patent
Liu et al.

(10) Patent No.: US 10,643,761 B2
(45) Date of Patent: May 5, 2020

(54) METHOD FOR EVALUATING IRRADIATION ANGLE OF BEAM

(71) Applicant: NEUBORON MEDTECH LTD., Nanjing, Jiangsu (CN)

(72) Inventors: Yuan-Hao Liu, Jiangsu (CN); Wei-Lin Chen, Jiangsu (CN)

(73) Assignee: NEUBORON MEDTECH LTD., Nanjing, Jiangsu (CN)

(*) Notice: Subject to any disclaimer, the term of this patent is extended or adjusted under 35 U.S.C. 154(b) by 71 days.

(21) Appl. No.: 15/991,290

(22) Filed: May 29, 2018

(65) Prior Publication Data
US 2018/0277278 A1    Sep. 27, 2018

Related U.S. Application Data

(63) Continuation of application No. PCT/CN2016/102312, filed on Oct. 18, 2016.

(30) Foreign Application Priority Data

Dec. 8, 2015  (CN) .......................... 2015 1 0894752

(51) Int. Cl.
*G21K 5/04* (2006.01)
*A61N 5/10* (2006.01)

(52) U.S. Cl.
CPC ................. *G21K 5/04* (2013.01); *A61N 5/10* (2013.01); *A61N 5/1031* (2013.01);
(Continued)

(58) Field of Classification Search
CPC . A61N 5/00; A61N 5/022; A61N 5/01; A61N 5/1065; A61N 5/1067;
(Continued)

(56) References Cited

U.S. PATENT DOCUMENTS 5,341,292 A   8/1994  Zamenhof
5,976,066 A  11/1999  Yanch et al.
(Continued)

FOREIGN PATENT DOCUMENTS

CN   101014383 A   8/2007
CN   101663069 A   3/2010
(Continued)

OTHER PUBLICATIONS

International Search Report of PCT/CN2016/102312, dated Jan. 6, 2017.

*Primary Examiner* — Jason L McCormack
(74) *Attorney, Agent, or Firm* — Locke Lord LLP; Tim Tingkang Xia, Esq.

(57) ABSTRACT

Disclosed is a method for evaluating an irradiation angle of a beam, including a step of sampling the irradiation angle of the beam, wherein the irradiation angle of the beam is defined as being the direction of the vector of the irradiation point of the beam to the pre-set point of the tumor; and a step of calculating the track of the beam passing through the organs, wherein it is determined whether the tumor is fully covered within the effective treatment depth, and if so, entering the steps of calculating the evaluation coefficient, recording the irradiation conditions and calculating the results, and returning to the step of sampling the irradiation angle of the beam; and if not, entering the step of giving the worst evaluation coefficient and returning to the step of sampling the irradiation angle of the beam.

19 Claims, 2 Drawing Sheets

(52) U.S. Cl.
 CPC ...... *A61N 5/1077* (2013.01); *A61N 2005/109* (2013.01); *G06T 2207/10072* (2013.01); *G06T 2207/30096* (2013.01)

(58) Field of Classification Search
 CPC .... A61N 5/1069; A61N 5/107; A61N 5/1071; A61N 5/1072; A61N 5/1074; A61N 5/1076; A61N 5/1078; A61N 5/1081; A61N 5/1087
 USPC ............................... 250/492.1, 492.3, 493.1
 See application file for complete search history.

(56) References Cited

U.S. PATENT DOCUMENTS

| | | | |
|---|---|---|---|
| 2007/0034812 A1* | 2/2007 | Ma | A61N 5/1031 250/492.21 |
| 2008/0310590 A1 | 12/2008 | Meyer et al. | |
| 2009/0168960 A1* | 7/2009 | Jongen | A61N 5/1049 378/65 |
| 2013/0033700 A1* | 2/2013 | Hallil | G01B 11/00 356/72 |

FOREIGN PATENT DOCUMENTS

| | | |
|---|---|---|
| CN | 102068763 A | 5/2011 |
| CN | 103083820 A | 5/2013 |
| CN | 104338244 A | 2/2015 |
| TW | 201538200 A | 10/2015 |
| WO | 2005057738 A2 | 6/2005 |
| WO | 2011042819 A1 | 4/2011 |

* cited by examiner

METHOD FOR EVALUATING IRRADIATION ANGLE OF BEAM

RELATED APPLICATION INFORMATION

This application is a continuation of International Application No. PCT/CN2016/102312, filed on Oct. 18, 2016, which claims priority to Chinese Patent Application No. 201510894752.1, filed on Dec. 8, 2015, the disclosures of which are hereby incorporated by reference.

FIELD OF THE DISCLOSURE

The present disclosure relates to a method for evaluating irradiation angle, and, more particularly, to a method for evaluating irradiation angle of beam.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIGS. 1 and 2, a schematic drawing of BNCT and a nuclear reaction formula of $^{10}B$ (n, α) $^7Li$ neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7Li$ are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

In the existing neutron capture treatment planning system, the geometric angle of irradiation is determined and defined artificially based on experience. Due to the structure of the human body is quite complex and the sensitivity of various tissues or organs to radiation is also different. Therefore, a better angle of irradiation is likely to be ignored by relying on human judgment only, resulting in poor therapeutic effect. In order to achieve the optimization of the therapeutic effect, the irradiation angle of the beam is an essential part to be considered.

Therefore, it is necessary to propose a method for evaluating the irradiation angle of a beam.

The statements in this section merely provide background information related to the present disclosure and may not constitute prior art.

SUMMARY

In order to overcome defects of prior art, the inventor of the present disclosure developed an executable method for optimizing the irradiation angle, which can be used as a favorable reference, and in combination with doctor's experience, for finding out the best irradiation angle as far as possible. Implementation of the routing optimization is carried out by assigning multiple lines of tracks from the tumor to the body surface, and calculating the evaluation coefficient of individual track taking into account the proportion of organs in the track and their radiation sensitive coefficients, by a forward calculation method (from the body surface to the tumor) or a reverse calculation method (from the tumor to the body surface) with selecting points sequentially or randomly. Through the above method, the evaluation score for the incidence into the tumor from each point on the surface can be calculated, which can be fused with 2D or 3D images to help the user find the best point of incidence.

Specifically, in one aspect, the present disclosure provides a method for evaluating an irradiation angle of a beam, including: a step of sampling the irradiation angle of the beam, wherein the irradiation angle of the beam is defined as being the vector direction from an irradiation point of the beam to a pre-set point of a tumor; and a step of calculating the track of the beam passing through an organ, wherein it is determined whether the tumor is fully covered within the effective treatment depth: if yes, entering steps of calculating an evaluation coefficient, recording irradiation conditions and calculating results, and returning to the step of sampling the irradiation angle of the beam; and if not, entering a step of giving a worst evaluation coefficient and returning to the step of sampling the irradiation angle of the beam.

According to the method for evaluating the irradiation angle of the beam, it can be clearly recognized whether the performance of the beam irradiating at a certain position and at a certain angle is good or bad, thus providing strong data support for the doctor or the physicists to decide on the irradiation mode.

The "pre-set point of the tumor" can be set as the centroid of the tumor or the deepest point in the tumor, and the location of the specific pre-set point of the tumor can be adjusted according to the user's needs. As preferred, the irradiation angle of the beam is defined as the vector direction from the irradiation point of the beam to the centroid of the tumor or the deepest point in the tumor. Certainly, it is well known to those skilled in the art that the irradiation angle of the beam can also be customized according to user's needs.

Certainly, it is well known to those skilled in the art that the above vector direction includes the direction of the positive vector from the irradiation point of the beam to the pre-set point of the tumor, and the direction of the negative vector.

Implementations of this aspect may include one or more of the following features.

More particularly, the beam is one or more selected from the group consisting of a neutron beam, a charged particle beam, or a gamma ray, wherein the charged particle beam can be an electron beam, a proton beam, and a heavy particle beam.

In order to more accurately calculate the evaluation coefficient, calculating the evaluation coefficient based on the beam characteristics, the radiation sensitivity coefficient, and the boron concentration of an organ.

in the sampled irradiation angle and irradiation track, a weighting factor (W(i)) of the organ (i) is calculated using the formula I:

$$W(i)=I(i) \times S(i) \times C(i) \qquad \text{(Formula I)}$$

Wherein, I(i), S(i) and C(i) are the beam intensity, the radiation sensitive coefficient of the organ (i) and the boron concentration of the organ (i), respectively.

Further, the I(i) is calculated using Formula II that integrates the depth intensity or dose curve of the human body according to the beam used:

$$I(i)=\int_{x_0}^{x} i(x)dx \qquad \text{(Formula II)}$$

Wherein i(x) is the depth intensity or dose curve function of a therapeutic beam in an approximate human body and $x_0$-x is the depth range of the organ (i) in a beam track.

The evaluation coefficient is calculated using Formula III:

$$Q(x, y, z, \phi, \theta) = \sum_i W(i) \qquad \text{(Formula III)}$$

Wherein Q(x, y, z, Φ, θ) as the evaluation coefficient is the sum of the weighting factors of each organ in the organ track.

Certainly, another way of presenting the evaluation coefficient, that is, the ratio of organ evaluation coefficient to tumor evaluation coefficient, can also be used.

The ratio (QR(x, y, z, Φ, θ)) of the evaluation coefficient to the tumor evaluation coefficient is calculated using Formula IV:

$$QR(x, y, z, \phi, \theta) = \sum_i W(i)/W(\text{tumor}) \qquad \text{(Formula IV)}$$

Wherein, W(tumor) is the weighting factor of the tumor.

The "medical image data" may be Magnetic Resonance Imaging (MRI) or Computed Tomography (CT) or Positron Emission computed Tomography (PET-CT). However, it is well known to those skilled in the art that other medical image data can also be used as long as the medical image data can define the materials and densities of organs, tissues and tumors, it can be applied to the method for evaluating the irradiation angle of the beam disclosed in the present disclosure. As preferred, the step of reading medical image data is a step of reading at least one kind of medical image data selected from the group consisting of CT image data, MRI image data, or PET-CT image data.

"Organ track" refers to a beam track through skin, bone, tissue and tumor when irradiated a beam at a certain position and at a certain angle. For example, the organ track is a track of a beam sequentially passing through the skin, bone, tissue, tumor, tissue, bone, and skin. In some calculations, for example, when the weighting factors of the organs are added to a total, the weighting factor of the tumor may not be included. As preferred, the organ track is a track of a beam sequentially through the skin, skull, brain tissue, tumor, brain tissue, skull, and skin. This clearly shows the track of the beam through the brain. Certainly, it is well known to those skilled in the art that the organ track may be a beam sequentially through other part of the human body other than the brain, for example, the liver.

As preferred, the method for evaluating the irradiation angle of the beam further includes a step of displaying each evaluation coefficient in a 3D image. Certainly, those skilled in the art can also display each evaluation coefficient in other ways, as long as the doctor or the physicists can identify each evaluation coefficient displayed.

The "beam" may be one or more radioactive beams. Preferably, the beam is a mixed beam of neutron beam and gamma beam, or may be an individual neutron beam, an individual proton beam or an individual heavy particle beam.

The method for evaluating the irradiation angle of the beam further includes a step of reading the medical image data; a step of defining or reading the profile of an organ, tissue and tumor; and a step of defining the material and the density of the organ, tissue and tumor.

In another aspect of the present disclosure provides a method for evaluating an irradiation angle of a beam, includes: a step of sampling the irradiation angle of the beam, wherein the beam angle can be sampled at random intervals or at specified intervals; and a step of calculating the track of the beam passing through an organ, wherein it is determined whether the tumor is fully covered within the effective treatment depth: if yes, entering steps of calculating an evaluation coefficient, recording irradiation conditions and calculating results, and returning to the step of sampling the irradiation angle of the beam; and if not, entering a step of giving a worst evaluation coefficient and returning to the step of sampling the irradiation angle of the beam.

More particularly, the beam is one or more selected from the group consisting of a neutron beam, a charged particle beam, or a gamma ray.

More particularly, calculating the evaluation coefficient based on the beam characteristics, the radiation sensitivity coefficient, and the boron concentration of an organ.

More particularly, in the sampled irradiation angle and irradiation track, the weighting factor (W(i)) of the organ (i) is calculated using the formula I:

$$W(i)=I(i) \times S(i) \times C(i) \qquad \text{(Formula I)}$$

Wherein, I(i), S(i) and C(i) are the beam intensity, the radiation sensitive coefficient of the organ (i) and the boron concentration of the organ (i), respectively.

More particularly, the I(i) is calculated using Formula II that integrates the depth intensity or dose curve of the human body according to the beam used:

$$I(i)=\int_{x_0}^{x} i(x)dx \qquad \text{(Formula II)}$$

Wherein i(x) is the depth intensity or dose curve function of a therapeutic beam in an approximate human body and $x_0$-x is the depth range of the organ (i) in a beam track.

More particularly, the evaluation coefficient is calculated using Formula III:

$$Q(x, y, z, \phi, \theta) = \sum_i W(i) \qquad \text{(Formula III)}$$

Wherein Q(x, y, z, Φ, θ) as the evaluation coefficient is the sum of the weighting factors of each organ in the organ track.

More particularly, the ratio (QR(x, y, z, Φ, θ)) of the evaluation coefficient to the tumor evaluation coefficient is calculated using Formula IV:

$$QR(x, y, z, \phi, \theta) = \sum_i W(i)/W(\text{tumor}) \qquad \text{(Formula IV)}$$

Wherein, W(tumor) is the weighting factor of the tumor.

More particularly, the method for evaluating the irradiation angle of the beam further includes a step of reading the medical image data; a step of defining or reading the profile of an organ, tissue and tumor; and a step of defining the material and the density of the organ, tissue and tumor.

In yet another aspect of the present disclosure provides a method for evaluating an irradiation angle of a beam, includes: a step of reading the medical image data; a step of defining or reading the profile of an organ, tissue and tumor; a step of sampling the irradiation angle of the beam; and a step of calculating the track of the beam passing through the organ, wherein it is determined whether the tumor is fully covered within the effective treatment depth: if yes, entering steps of calculating an evaluation coefficient, recording irradiation conditions and calculating results, and returning to the step of sampling the irradiation angle of the beam; and if not, entering a step of giving a worst evaluation coefficient and returning to the step of sampling the irradiation angle of the beam.

More particularly, calculating the evaluation coefficient based on the beam characteristics, the radiation sensitivity coefficient, and the boron concentration of an organ.

Other advantages, objects, and features of the disclosure will be apparent to those skilled in the art from the following description, taken in part by the research and practice of the disclosure.

Further areas of applicability will become apparent from the description provided herein. It should be understood that the description and specific examples are intended for purposes of illustration only and are not intended to limit the scope of the present disclosure.

Figure 1:
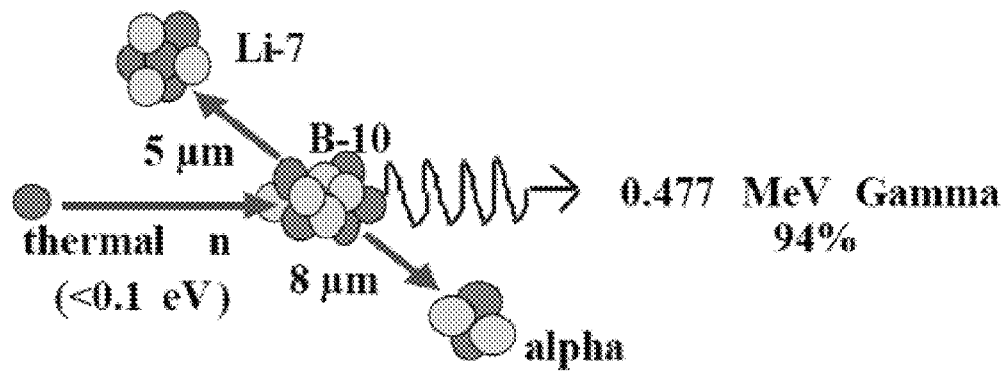
FIG. 1 is a boron neutron capture reaction schematic.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

The present disclosure will now be described in further detail with reference to the accompanying drawings in order to enable those skilled in the art to practice with reference to the specification.

The embodiments of the present disclosure are further described in detail below with reference to the accompanying drawings, so that those skilled in the art can implement the technical solutions according to the description.

As preferred, a method for evaluating the irradiation angle of a beam for neutron capture therapy is taken as an embodiment of the present disclosure. The following will briefly introduce neutron capture therapy, especially boron neutron capture therapy.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li$ (p, n) $^7Be$ and $^9Be$ (p, n) $^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

Figure 2:
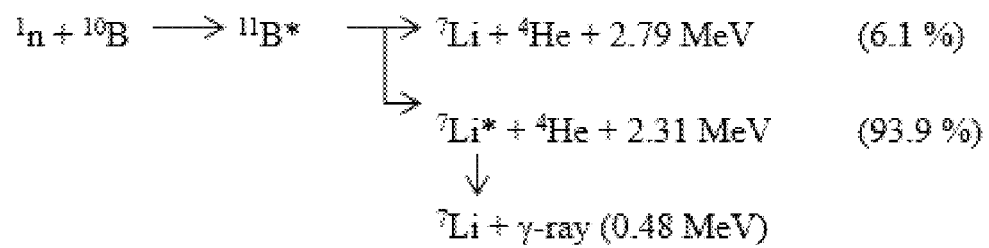
FIG. 2 is a $^{10}B(n,\alpha)$ $^7Li$ neutron capture nuclear reaction formula.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIGS. 1 and 2, a schematic drawing of BNCT and a nuclear reaction formula of $^{10}B$ (n, α) $^7Li$ neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7Li$ are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>1×10$^9$ n/cm$^2$ s
Fast neutron contamination<2×10$^{-13}$ Gy–cm$^2$/n
Photon contamination<2×10$^{-13}$ Gy–cm$^2$/n
Thermal to epithermal neutron flux ratio<0.05
Epithermal neutron current to flux ratio>0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by Gy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time<=30 min (proton current for accelerator is 10 mA)
2. 30.0 RBE-Gy treatable depth>=7 cm
3. The maximum tumor dose>=60.0 RBE-Gy
4. The maximum dose of normal brain tissue<=12.5 RBE-Gy
5. The maximum skin dose<=11.0 RBE-Gy Note: RBE stands for relative biological effectiveness. Since photons and neutrons express different biological effectiveness, the dose above should be multiplied with RBE of different tissues to obtain equivalent dose.

Figure 3:
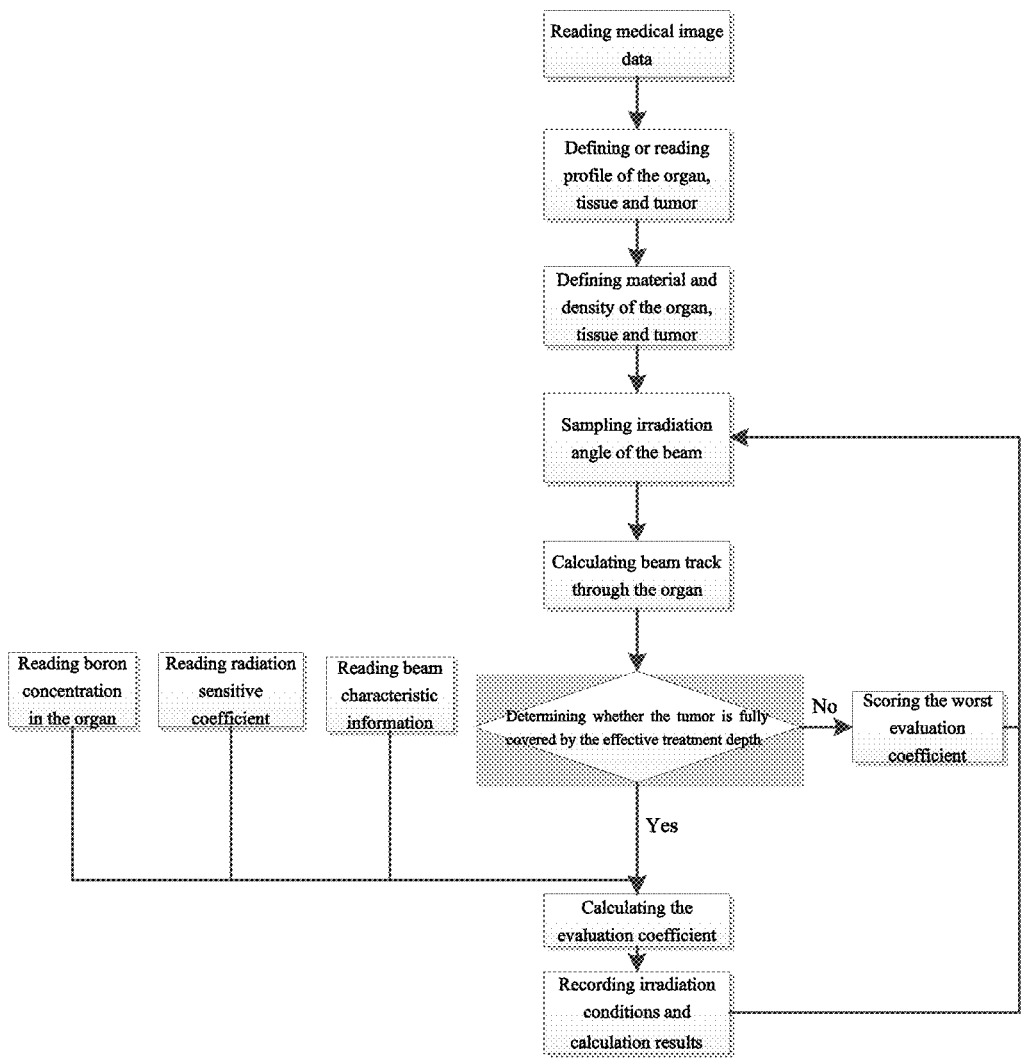
FIG. 3 is a logic block diagram of the method for evaluating the irradiation angle of a beam in an embodiment of the present disclosure.
Figure 4:
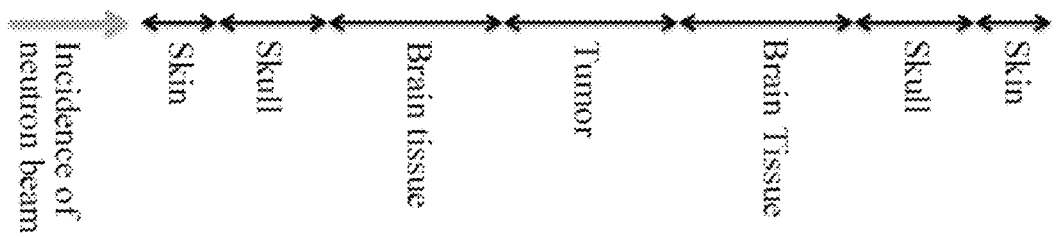
FIG. 4 is a schematic diagram of an organ track when a beam is irradiated according to an embodiment of the present disclosure.

Please refer to FIG. 3 and FIG. 4, in order to provide reference basis for the irradiation angle of the beam for neutron capture therapy, in the following, each possible irradiation angle was calculated by random or one by one, and the evaluation coefficients were calculated by Formula I and Formula II, and each evaluation coefficient was displayed as a 3D image, which is convenient for the doctor or physician to judge the irradiation angle of the treatment.

The establishment step of the 3D evaluation coefficient image will be described in detail below, which is a preferred implementation step, and it is well known to those skilled in the art that it is not necessary to follow the preferred implementation step. Specifically, the step is: read the images of patients with definite human anatomy, such as CT/MRI/PET-CT, to define the profile of each organ, tissue and tumor one by one, and to assign the type and density of the material. After the completion of the definition of the geometric material and the density, it is decided to calculate the starting position and the angle of the beam. The determination of the starting position and angle in the calculation can be a forward algorithm or a reverse algorithm. In the forward algorithm, the starting position is determined in an in-vitro position and can be sampled sequentially at a fixed angle or distance interval, or sampled randomly; regarding the beam angle, it can be set as the vector direction from the irradiation point of the beam to the centroid of the tumor or the deepest point in the tumor, and the location of the specific endpoint of the tumor can be adjusted according to user's needs. In the reverse algorithm, the starting position is determined in the range of a tumor, and the starting position can be the tumor centroid, the deepest or a random point within the tumor, and the beam angle can be sampled at random intervals or at specified intervals. After the position and angle of the beam are decided, the organ track through which the beam axis passes is calculated, that is, the type and thickness of the organ which the beam passes after entering the human body are calculated. After obtaining the track information of the beam axis passing through the human body, it is judged whether the tumor range falls within the maximum treatable depth range. If yes, then based on this track information, the evaluation coefficient of the track is calculated according to the boron concentration in the organ, the radiation sensitive coefficient of the organ and the beam characteristic information set by the user; If not, a worst evaluation coefficient is scored, and the beam position and irradiation angle are re-sampled. After the calculation of the evaluation coefficient is completed, the record of the irradiation position, angle and evaluation coefficient is performed. After a certain number of calculations are repeated, the report can be output and provided to the doctor or physician as a reference to determine the irradiation pattern. The data can also be expressed in the form of 3D images to more conveniently judge the pros and cons based on the evaluation coefficients around the beam axis.

The evaluation coefficient is calculated based on the beam characteristics, the organ radiation sensitive coefficient and the boron concentration in the organ. Corresponding to a position and an irradiation track, the weighting factor (W(i)) of organ i is calculated as shown in Formula I, wherein, I(i), S(i) and C(i) are the beam intensity, the radiation sensitive coefficient of the organ i and the boron concentration of the organ i, respectively.

$$W(i)=I(i) \times S(i) \times C(i) \qquad \text{(Formula I)}$$

Wherein, the I(i) is obtained by integrating the depth intensity or dose curve of the human body according to the beam used, as shown in Formula II. In the formula, i(x) is the depth intensity or dose curve function of the therapeutic beam in an approximate human body and $x_0$-x is the depth range of the organ i in the beam track.

$$I(i)=\int_{x_0}^{x} i(x)dx \qquad \text{(Formula II)}$$

Through the above algorithm, the weighting factors of each organ in the organ track are sequentially calculated and then summed up to obtain the evaluation coefficient corresponding to the beam, as shown in Formula III. In this calculation, the weighting factor of the tumor should not be included in the calculation.

$$Q(x, y, z, \phi, \theta) = \sum_{i} W(i) \qquad \text{(Formula III)}$$

According to the level of the above evaluation coefficient, the degree of damage to the normal tissue during the treatment can be more intuitively determined. In addition to the evaluation coefficient, the evaluation ratio coefficient can also be used to evaluate the irradiation position and angle, which is defined as a ratio of the evaluation coefficient to the weighting factor of the tumor, as shown in Formula IV. In this way, the expected therapeutic effect of the irradiation position and angle can be more fully revealed.

$$QR(x, y, z, \phi, \theta) = \sum_{i} W(i)/W(\text{tumor}) \qquad \text{(Formula IV)}$$

The steps involved in the above embodiments—to read the images of patients with definite human anatomy, such as CT/MRI/PET-CT, to define the profile of each organ, tissue and tumor one by one, and to assign the type and density of the material—may refer to the patent application filed by the applicant on Jan. 17, 2015 to the State Intellectual Property Office with the application No. 201510790248.7 and entitled "Geometric Model Establishment Method Based on Medical Image Data", which is hereby incorporated by reference in its entirety.

It is well known to persons skilled in the art that some simple transformations in the above Formula I to Formula IV are still within the claimed scope of the present disclosure, for example, the multiplication of I(i), S(i) and C(i) changes to addition; I(i), S(i) and C(i) are respectively multiplied by the n-th power, n may be an integer multiple of 1 or other multiplicities, depending on the situation; i(x) may be the average or the medium of $x_0$-x times ($x_0$-x), or any calculation method that can achieve matching to the result of intensity integral calculation.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A method for evaluating an irradiation angle of a beam, comprising:
    sampling the irradiation angle of the beam, wherein the irradiation angle of the beam is defined by a vector direction from an irradiation point of the beam to a pre-set point of a tumor;
    calculating a track of the beam passing through organs of a human patient based on the irradiation angle of the beam;
    determining, based on the track of the beam, whether the tumor is fully covered within an advantage depth;
    in response to determining that the tumor is fully covered within the advantage depth, calculating an evaluation coefficient of the track, recording irradiation conditions and calculating results; and
    in response to determining that the tumor is not fully covered within the advantage depth, assigning a specific evaluation coefficient value as the evaluation coefficient of the track.

2. The method according to claim 1, wherein the beam is one or more selected from the group consisting of a neutron beam, a charged particle beam, or a gamma ray.

3. The method according to claim 1, wherein the evaluation coefficient of the track is calculated based on beam characteristics, a radiation sensitivity coefficient of each of the organs, and the boron concentration of the organs.

4. The method according to claim 3, further comprising:
    in the sampled irradiation angle and the track of the beam, calculating a weighting factor (W(i)) of each specific organ (i) of the organs using formula I:

$$W(i)=I(i) \times S(i) \times C(i) \qquad \text{(Formula I)}$$

wherein I(i) is an intensity of the beam, S(i) is the radiation sensitivity coefficient of each specific organ (i), and C(i) is the boron concentration of each specific organ (i).

5. The method according to claim 4, wherein the I(i) is calculated by an integral of a depth intensity or dose curve of a body of the human patient according to the beam using Formula II:

$$I(i)=\int_{x_0}^{x} i(x)dx \quad \text{(Formula II)}$$

wherein i(x) is a function of the depth intensity or the dose curve of a therapeutic beam in an approximate human body, and $x_0$-x is a depth range of each specific organ (i) in the track of the beam.

6. The method according to claim 4, wherein the evaluation coefficient of the track is calculated using Formula III:

$$Q(x, y, z, \phi, \theta) = \sum_i W(i) \quad \text{(Formula III)}$$

wherein Q(x, y, z, Φ, θ) as the evaluation coefficient is a sum of the weighting factors of the organs in the track of the beam.

7. The method according to claim 6, wherein a ratio (QR(x, y, z, Φ, θ)) of the evaluation coefficient of the track to a tumor evaluation coefficient is calculated using Formula IV:

$$QR(x, y, z, \phi, \theta) = \sum_i W(i)/W(\text{tumor}) \quad \text{(Formula IV)}$$

wherein W(tumor) is a weighting factor of the tumor.

8. The method according to claim 1, further comprising: reading a medical image data selected from the group consisting of CT image data, MRI image data, or PET-CT image data.

9. The method according to claim 1, further comprising: displaying the evaluation coefficient of the track in a 3D image.

10. The method according to claim 1, comprising:
reading medical image data;
defining or reading profiles of the organs and the tumor; and
defining a material and a density of each of the organs and the tumor.

11. A method for evaluating a plurality of irradiation angles of a beam, comprising:
selecting, from the plurality of irradiation angles, a specific irradiation angle; and
evaluating the specific irradiation angle using the method according to claim 1.

12. The method according to claim 11, further comprising:
displaying, for each of the plurality of irradiation angle being evaluated, the evaluation coefficient of the track of the beam in a 3D image.

13. The method according to claim 11, wherein the specific irradiation angle is selected from the plurality of irradiation angles randomly.

14. The method according to claim 11, wherein for each of the plurality of irradiation angles being evaluated, the evaluation coefficient of the track is calculated based on beam characteristics, a radiation sensitivity coefficient of each of the organs, and the boron concentration of the organs.

15. The method according to claim 14, further comprising:
for each of the plurality of irradiation angles being evaluated, in the sampled irradiation angle and the track of the beam, calculating a weighting factor (W(i)) of each specific organ (i) of the organs using Formula I:

$$W(i)=I(i)\times S(i)\times C(i) \quad \text{(Formula I)}$$

wherein I(i) is an intensity of the beam, S(i) is the radiation sensitivity coefficient of each specific organ (i), and C(i) is the boron concentration of each specific organ (i).

16. The method according to claim 15, wherein the I(i) is calculated by an integral of a depth intensity or dose curve of a body of the human patient according to the beam using Formula II:

$$I(i)=\int_{x_0}^{x} i(x)dx \quad \text{(Formula II)}$$

wherein i(x) is a function of the depth intensity or the dose curve of a therapeutic beam in an approximate human body, and $x_0$-x is a depth range of each specific organ (i) in the track of the beam.

17. The method according to claim 15, wherein the evaluation coefficient of the track is calculated using Formula III:

$$Q(x, y, z, \phi, \theta) = \sum_i W(i) \quad \text{(Formula III)}$$

wherein Q(x, y, z, Φ, θ) as the evaluation coefficient is a sum of the weighting factors of the organs in the track of the beam.

18. The method according to claim 17, wherein a ratio (QR(x, y, z, Φ, θ)) of the evaluation coefficient of the track to a tumor evaluation coefficient is calculated using Formula IV:

$$QR(x, y, z, \phi, \theta) = \sum_i W(i)/W(\text{tumor}) \quad \text{(Formula IV)}$$

wherein W(tumor) is a weighting factor of the tumor.

19. The method according to claim 11, further comprising:
reading medical image data, wherein the medical image data is selected from the group consisting of CT image data, MRI image data, or PET-CT image data;
defining or reading profiles of the organs and the tumor; and
defining a material and a density of each of the organs and the tumor.

* * * * *